(12) United States Patent
Zawacki et al.

(10) Patent No.: US 8,226,632 B2
(45) Date of Patent: Jul. 24, 2012

(54) CONNECTION METHODS (75) Inventors: John A. Zawacki, Salt Lake City, UT (US); Jeffrey A. Vasek, Goleta, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 456 days.

(21) Appl. No.: 11/295,741

(22) Filed: Dec. 5, 2005

(65) Prior Publication Data
US 2006/0127165 A1    Jun. 15, 2006

Related U.S. Application Data (63) Continuation of application No. 10/071,378, filed on Feb. 5, 2002, now Pat. No. 6,971,390.

(51) Int. Cl.
*A61M 25/16* (2006.01)
*F16L 33/00* (2006.01)
*F16L 47/00* (2006.01)
*F16L 49/00* (2006.01)

(52) U.S. Cl. ......................... 604/533; 285/245
(58) Field of Classification Search .................. 604/533
See application file for complete search history.

(56) References Cited

U.S. PATENT DOCUMENTS

| 787,529 A * | 4/1905 | Muehlberg ..................... 285/246 |
| 2,704,074 A | 3/1955 | Butler |
| 3,408,099 A * | 10/1968 | Appleton ....................... 285/247 |
| 4,278,279 A * | 7/1981 | Zimmerman ................. 285/255 |
| 4,547,194 A | 10/1985 | Moorehead |
| 4,583,767 A * | 4/1986 | Hansen ............................ 285/40 |
| 4,749,217 A * | 6/1988 | Causby et al. ................. 285/245 |
| 4,772,270 A | 9/1988 | Wiita et al. |
| 4,772,276 A | 9/1988 | Wiita et al. |
| 4,826,477 A | 5/1989 | Adams |
| 4,880,414 A * | 11/1989 | Whipple ........................ 604/533 |
| 4,903,995 A * | 2/1990 | Blenkush et al. ............... 285/38 |
| 4,929,236 A | 5/1990 | Sampson |
| 4,946,200 A * | 8/1990 | Blenkush et al. ............... 285/38 |
| 5,026,344 A * | 6/1991 | Dijkstra et al. ........... 604/288.02 |
| 5,178,423 A * | 1/1993 | Combeau ...................... 285/247 |
| 5,360,407 A | 11/1994 | Leonard |
| 5,399,168 A | 3/1995 | Wadsworth, Jr. et al. |
| 5,579,762 A | 12/1996 | Lee |
| 5,622,393 A | 4/1997 | Elbich et al. |
| 5,637,102 A * | 6/1997 | Tolkoff et al. ................. 604/536 |
| 5,833,654 A * | 11/1998 | Powers et al. ............... 604/93.01 |
| 6,003,906 A * | 12/1999 | Fogarty et al. ................ 285/242 |
| 6,113,572 A * | 9/2000 | Gailey et al. .............. 604/93.01 |
| 6,209,804 B1 * | 4/2001 | Spriegel ........................ 239/373 |

(Continued)

FOREIGN PATENT DOCUMENTS

GB    2257764    1/1993

(Continued)

*Primary Examiner* — Kevin C. Sirmons
*Assistant Examiner* — Andrew Gilbert
(74) *Attorney, Agent, or Firm* — Rutan & Tucker, LLP (57) ABSTRACT

Methods of coupling a catheter to a stem are disclosed. In some embodiments, a stem extends longitudinally between a proximal end and a distal end, and the stem can include at least one enlargement positioned between the proximal end and the distal end. In some embodiments, a catheter can be positioned over the at least one enlargement and over a region of the stem that is proximal to the at least one enlargement. In further embodiments, a collar can be mated to the stem.

19 Claims, 12 Drawing Sheets

U.S. PATENT DOCUMENTS

| | | | |
|---|---|---|---|
| 6,416,085 B1 * | 7/2002 | Markovic | 285/102 |
| 6,557,788 B1 * | 5/2003 | Huang | 239/600 |
| 6,641,177 B1 * | 11/2003 | Pinciaro | 285/242 |
| 7,163,531 B2 | 1/2007 | Seese et al. | |
| 7,300,430 B2 | 11/2007 | Wilson et al. | |
| 7,341,284 B2 * | 3/2008 | Mittersteiner et al. | 285/247 |

FOREIGN PATENT DOCUMENTS

| | | |
|---|---|---|
| WO | WO 93/17269 | 9/1993 |
| WO | 2006130133 A1 | 12/2006 |

* cited by examiner

CONNECTION METHODS

CROSS-REFERENCE TO RELATED APPLICATION

This application is a continuation of U.S. patent application Ser. No. 10/071,378, filed 5 Feb. 2002, now U.S. Pat. No. 6,971,390, the disclosure of which is incorporated, in its entirety, by this reference.

BACKGROUND

1. The Field of the Invention

The invention disclosed herein pertains to the art of effecting a fluid-tight coupling and a reliable mechanical joinder between a medical catheter and a coupling hub or other medical device that accommodates fluid flow therethrough. In particular, the invention as disclosed herein exhibits utility in relation to implantable cardiovascular access catheters as a system for repairing or extending such catheters or for attaching such catheters to a coupling hub or an outlet stem of an implantable vascular access port.

2. Background Art

Systems for securing medical catheters to medical devices that accommodate fluid flow are under continual redesign and refinement undertaken for the purposes of improving reliability, increasing ease of assembly, and accommodating for the development and adoption by the medical industry of new materials for medical catheters.

SUMMARY OF THE INVENTION

Accordingly, one object of the present invention is a catheter connection system having enhanced reliability, increased ease of assembly, or improved compatibility with medical catheters fabricated from newly developed materials, such as medical grade polyurethane.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a catheter connection system is disclosed that is capable of assembly without the use of adhesive. At a site of manufacture or in the field, a catheter connection system according to teachings of the present invention can be manipulated by a user into an assembled condition wherein the components of the catheter connection system are secured in a fluid-tight coupling and a reliable mechanical joinder to an end of a medical catheter.

As disclosed herein, a catheter connection system is provided that comprises an elongated catheter connection stem, a catheter securement collar, and grip enhancement means for constraining the outer wall of a catheter to traverse a tortuous path when the distal end of the connection stem is received in the lumen of the catheter and the securement collar and the connection stem are in the assembled condition of the connection system.

In one exemplary embodiment of structure capable of performing the function of the grip enhancement means, formed on the distal end of the connection stem is an enlargement that terminates at the proximal end thereof in a barrier wall that encircles the connection stem. Correspondingly, a catheter locking ring is provided on the interior of the securement collar at the distal end thereof. The locking ring is positioned proximal of the enlargement encircling the exterior of the connection stem in the assembled condition of the connection system.

According to further teachings of the present invention, various embodiments thereof are provided with attachment means for securing the proximal end of the securement collar in engagement with the exterior of the connection stem. Additionally provided may be translation means for advancing the securement collar in a proximal direction over the enlargement on the connection stem. An exemplary embodiment of structure capable of performing the functions of both the attachment means and the translation means includes a first set of threads on the exterior of the connection stem proximal of and remote from the enlargement thereon and a second set of threads on a portion of the inner bore of the securement collar that encircles and opposes the first set of threads on the connection stem in the assembled condition of the connection system. The second set of threads is configured to cooperate with the first set of threads in rotatingly advancing the securement collar proximally along the exterior of the connection stem into the assembled condition of the connection system.

According to yet another teaching of the present invention, a catheter system as described in whole or in part above is provided with purchase enhancement means for retaining a securement lip of catheter material from the outer wall of the catheter internal of the connection system in the assembled condition thereof. One embodiment of a structure capable of performing the function of the purchase enhancement means causes a void to be created internal of the connection system in the assembled condition thereof. The void is formed between the exterior surface of the connection stem and a purchase enhancement region of the internal bore through the engagement collar that is located between the distal end of the securement collar and the second set of threads. The internal diameter of the purchase enhancement region of the internal bore of the securement collar increases in a proximal direction longitudinally along the securement collar more rapidly than any increase in the outer diameter of the exterior of the connection stem opposite the purchase enhancement region.

In yet another aspect of the teachings of the present invention, a catheter connection system as described in part or in whole above is provided with pinching means for urging a portion of the outer wall of a catheter against the outer surface of the connection stem thereat to create longitudinally uniform conditions of maximum compression produced in the outer wall of the catheter by the connection system. In an exemplary embodiment of structure capable of performing the function of the pinching means, a cylindrical portion of the connection stem is provided adjacent to and proximal of the barrier wall of the enlargement thereupon. Correspondingly, the interior of the securement collar remote from the proximal end thereof is provided with a locking ring having a distal face that encircles the internal bore of the securement collar and a cylindrical interior surface adjacent to and proximal of the distal face. The radius of the interior surface of the locking ring is greater than the radius of the outer periphery of the barrier wall of the enlargement about the longitudinal axis of the connection stem, and the inner diameter of the internal bore of the securement collar is at a minimum at the locking ring. In the assembled condition of the connection system, the locking ring becomes positioned proximal of the shoulder of the enlargement, concentrically encircling the cylindrical portion of the connection stem.

BRIEF DESCRIPTION OF THE DRAWINGS

The manner in which the above-recited and other advantages and objects of the invention are obtained will be understood by a more particular description of the invention rendered by reference to specific embodiments thereof that are illustrated in the appended drawings. Understanding that these drawings depict only typical embodiments of the invention and are not therefore to be considered limiting of its scope, the invention will be described and explained with additional specificity and detail through the use of the accompanying drawings in which.

DESCRIPTION OF THE PREFERRED EMBODIMENT

Figure 1:
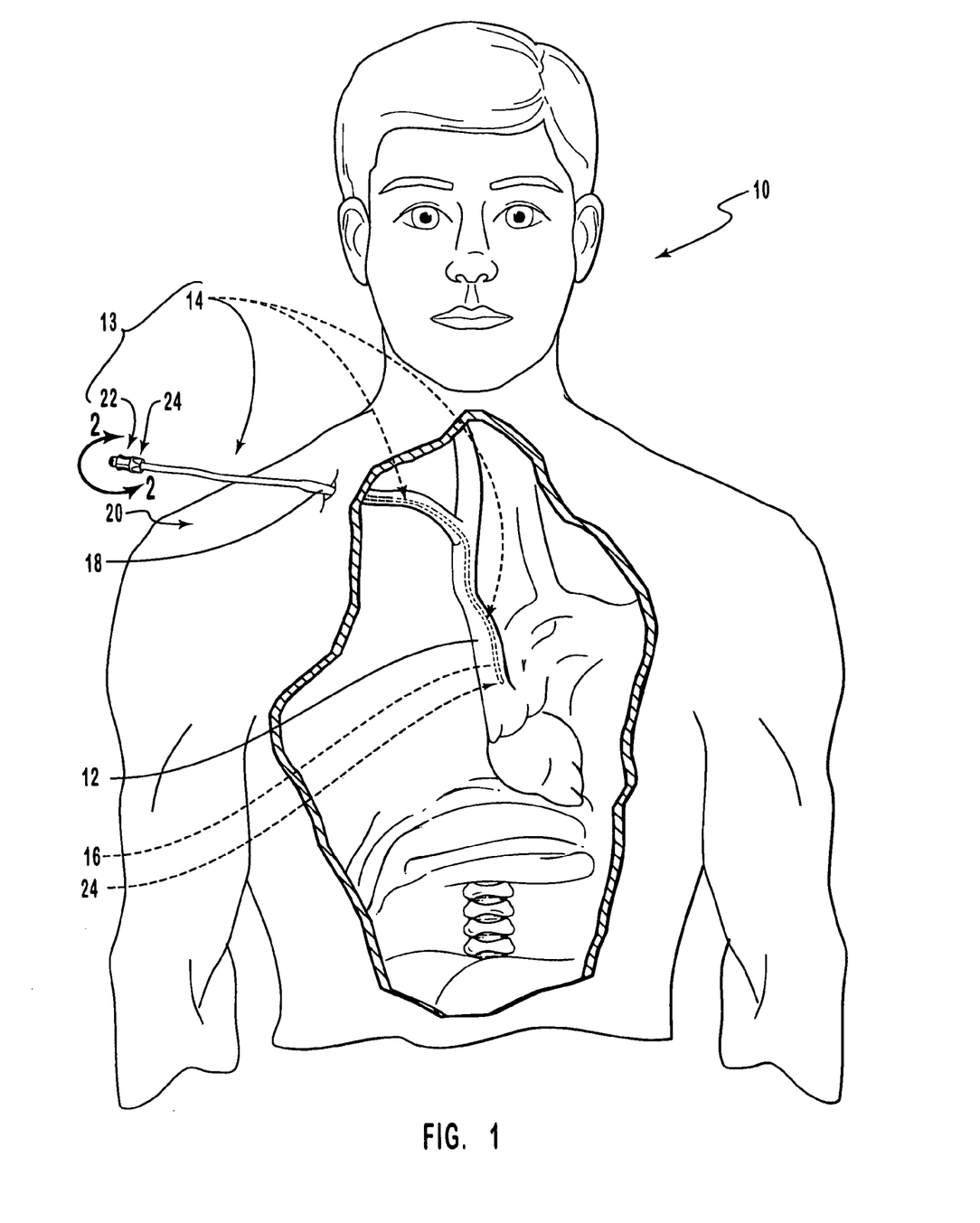
FIG. 1 is a perspective view of a cardiovascular access catheter device implanted in the body of a patient and including in the extracorporeal portion of the catheter device a first embodiment of a catheter connection system incorporating teachings of the present invention.

FIG. 1 depicts a patient 10 for whom a therapeutic procedure is to be undertaken on an intermittent basis in the superior vena cava 12 of the venous subsystem of the cardiovascular system. The required access to superior vena cava 12 is provided through the implantation of a catheter device 13 that includes a soft, biocompatible, single lumen vascular access catheter tube 14 having a distal portion 16 that is intended to reside in superior vena cava 12 and a proximal end 18 that exits the cardiovascular system and passes through the skin of patient 10 to the exterior of the body thereof in the vicinity of shoulder 20. Proximal end 18 of catheter tube 14 terminates in a coupling hub 22 that can be selectively coupled to extracorporeal medical equipment and that is secured in a fluid-tight coupling and a reliable mechanical joinder to proximal end 18 of catheter tube 14 utilizing a first embodiment of a catheter connection system 24 that incorporates teachings of the present invention.

Figure 2:
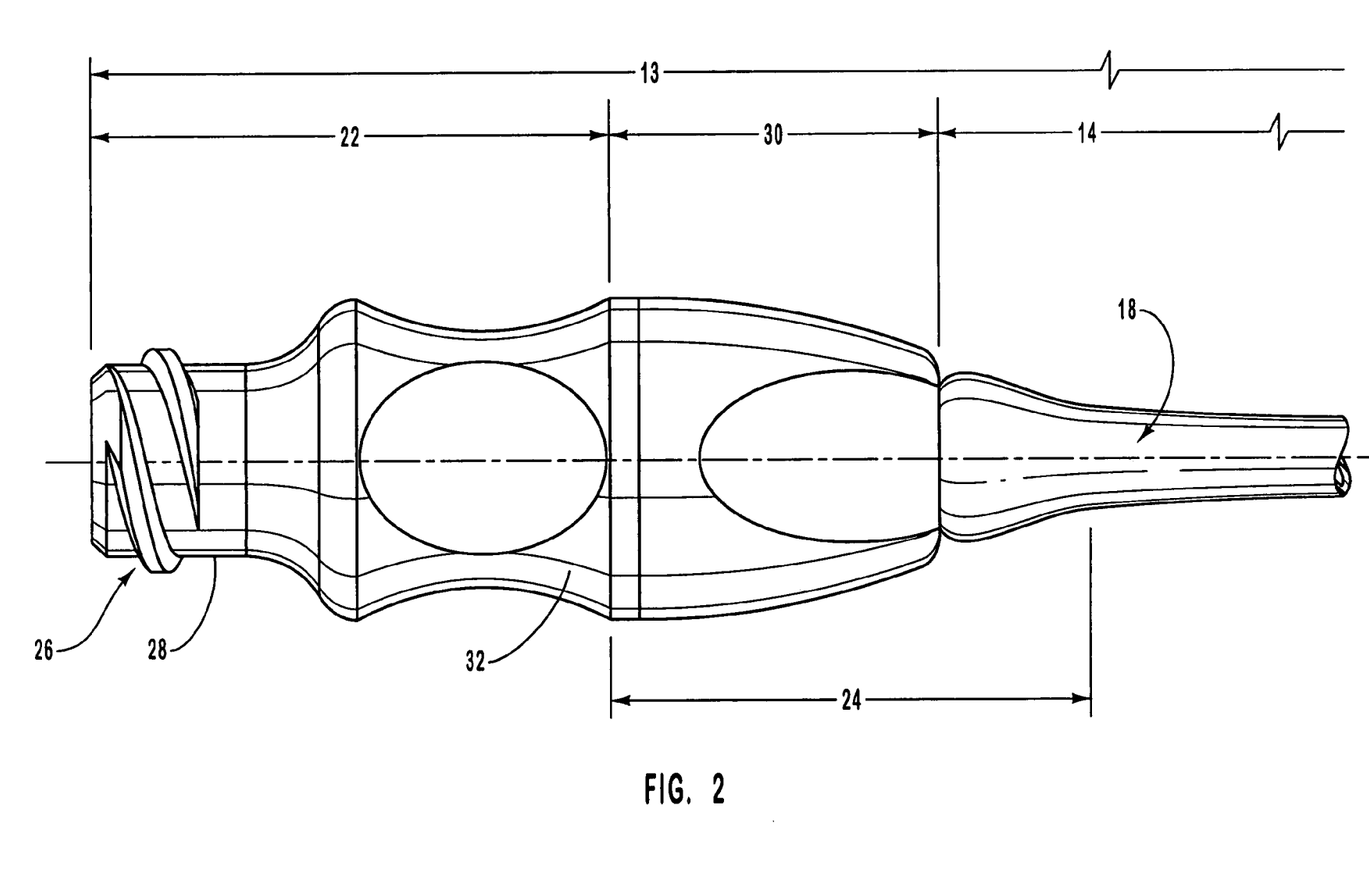
FIG. 2 is an enlarged plan view of the components of the catheter connection system of FIG. 1 in the assembled condition thereof and attached to the proximal end of the catheter tube of the catheter device of FIG. 1.

FIG. 2 illustrates in further detail coupling hub 22 and the elements of catheter connection system 24 that are secured to the proximal end 18 of catheter tube 14. Coupling hub 22 bears connection threads 26 for a standard threaded medical connector on proximal end 28 thereof. The sole component of catheter connection system 24 visible in FIG. 2 is a securement collar 30 that is positioned in abutment with the distal end 32 of coupling hub 22. Catheter tube 14, which extends from the end of securement collar 30 opposite from coupling hub 22, is attached in fluid-tight communication with a fluid passageway that extends longitudinally through catheter connection system 24 to proximal end 28 of coupling hub 22, but that is not visible in FIG. 2.

Each of the elements of catheter connection system 24 illustrated in FIG. 2 will be disclosed individually and in disassembled detail in relation to FIGS. 3-6.

Figure 3:
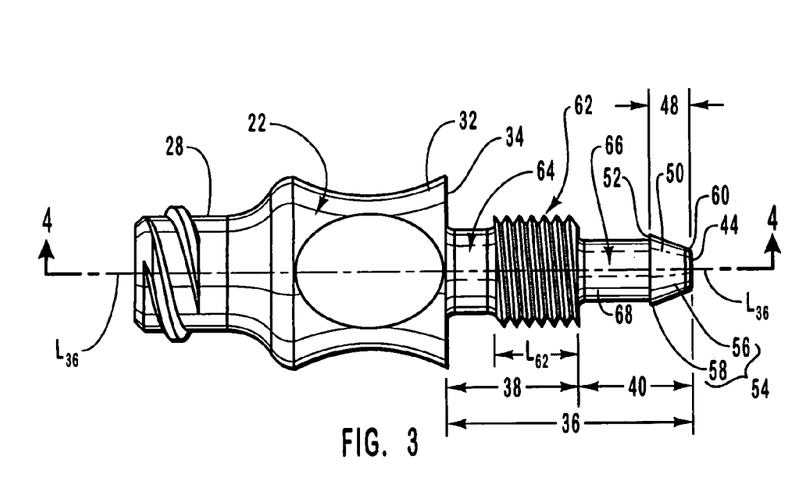
FIG. 3 is a plan view of the connection stem of the catheter connection system shown in FIG. 2.
Figure 4:
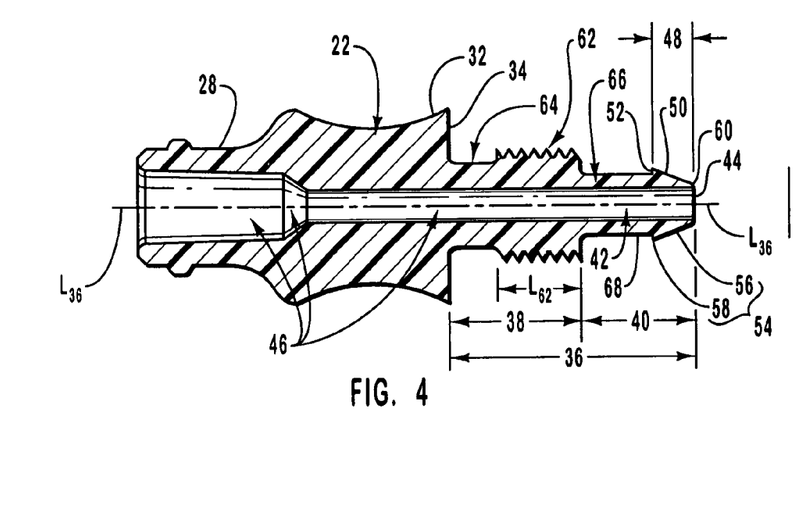
FIG. 4 is a longitudinal cross section of the connection stem shown in FIG. 3 taken along section line 4-4 therein.

FIGS. 3 and 4 taken together reveal that an elongated catheter connection stem 36 projects from distal end 32 of coupling hub 22. Connection stem 36 is attached at a proximal end 38 thereof to coupling hub 22 centrally of a distal face 34 on distal end 32 of coupling hub 22. The distal end 40 of catheter connection stem 36 is remote from coupling hub 22 and is configured to be receivable in the lumen of a catheter tube, such as catheter tube 14. Connection stem 36 encloses a fluid passageway 42 that extends between proximal end 38 thereof and the tip 44 of distal end 40. At a first end thereof, fluid passageway 42 communicates at proximal end 38 of connection stem 36 with a fluid passageway 46 in coupling hub 22. The opposite second end of fluid passageway 42 communicates with the exterior of connection stem 36 at tip 44 of distal end 40, which is positioned inside the lumen of catheter tube 14 in the assembled condition of catheter connection system 24 shown in FIG. 2.

Proximate to tip 44 of distal end 40, the exterior of connection stem 36 is formed into an enlargement 48 that terminates at a proximal end 50 thereof in a barrier wall 52. Barrier wall 52 encircles connection stem 36 and is oriented generally perpendicularly to the longitudinal axis $L_{36}$ of connection stem 36. Alternative configurations of an enlargement and an associated barrier wall for the distal end of a connection stem in a catheter connection system incorporating teachings of the present invention will be disclosed subsequently.

Enlargement 48 takes the particular form in catheter connection system 24 illustrated in FIGS. 3 and 4 of a frustoconical barb 54 formed on the exterior of distal end 40 of connection stem 36. The outer surface 56 of barb 54 enlarges radially outwardly about distal end 40 of connection stem 36 in a proximal direction to a shoulder 58 of barb 54, where barrier wall 52 terminates the proximal extent of barb 54. A rounded fillet 60 is interposed between outer surface 56 of barb 54 and tip 44 of distal end 40 of connection stem 36.

Between barb 54 and coupling hub 22 the exterior of connection stem 36 is encircled by a first set of threads 62 having a longitudinal extent $L_{36}$. First set of threads 62 is separated from distal face 34 of coupling hub 22 by a relatively large cylindrical section 64 and from barb 54 by a relatively smaller shaft 66. In the embodiment illustrated in FIGS. 3 and 4, shaft 66 has a cylindrical exterior surface 68 that is concentrically disposed about longitudinal axis $L_{36}$ of connection stem 36.

Figure 5:
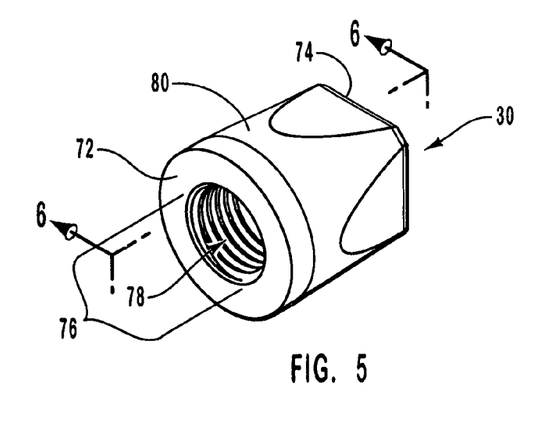
FIG. 5 is a perspective view of the securement collar of the catheter connection system shown in FIG. 2.

The second element of catheter connection system 24 is securement collar 30, which will be discussed in further detail in relation to FIGS. 5 and 6 taken together. In the embodiment illustrated, securement collar 30 is a circumferentially continuous tubular structure having a proximal face 72, a distal face 74, and an internal bore 76 extending therebetween. Internal bore 76 is sized to receive connection stem 36 and to advance proximally along the exterior thereof from tip 44 of distal end 40 into the assembled condition of catheter connection system 24 in which proximal face 72 of securement collar 30 abuts distal face 34 of coupling hub 22 and the longitudinal axis $L_{30}$ of securement collar 30 coincides with longitudinal axis $L_{36}$ of connection stem 36.

Figure 6:
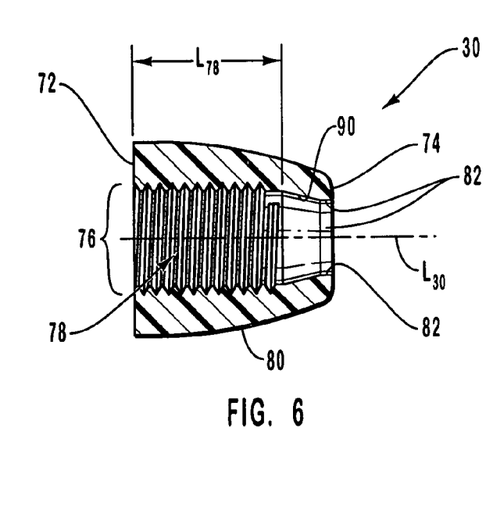
FIG. 6 is a longitudinal cross section of the securement collar of FIG. 5 taken along section line 6-6 therein.

As shown in FIG. 6, internal bore 76 is provided with a second set of threads 78 that is so configured to cooperate with first set of threads 62 in securing the proximal end of securement collar 30 in engagement with the exterior of connection stem 36. Second set of threads 78 extends to the proximal terminus of internal bore 76 at proximal face 72 of securement collar 30 and has a longitudinal extent $L_{78}$ that is greater than longitudinal extent $L_{62}$ of first set of threads 62. The outer profile 80 of securement collar 30 tapers radially inwardly from proximal face 72 to distal face 74 thereof, and the inner diameter of internal bore 76 distal of second set of threads 78 tapers radially inwardly to a locking ring 82 where internal bore 76 is of minimum diameter.

Figures 7, 7A:
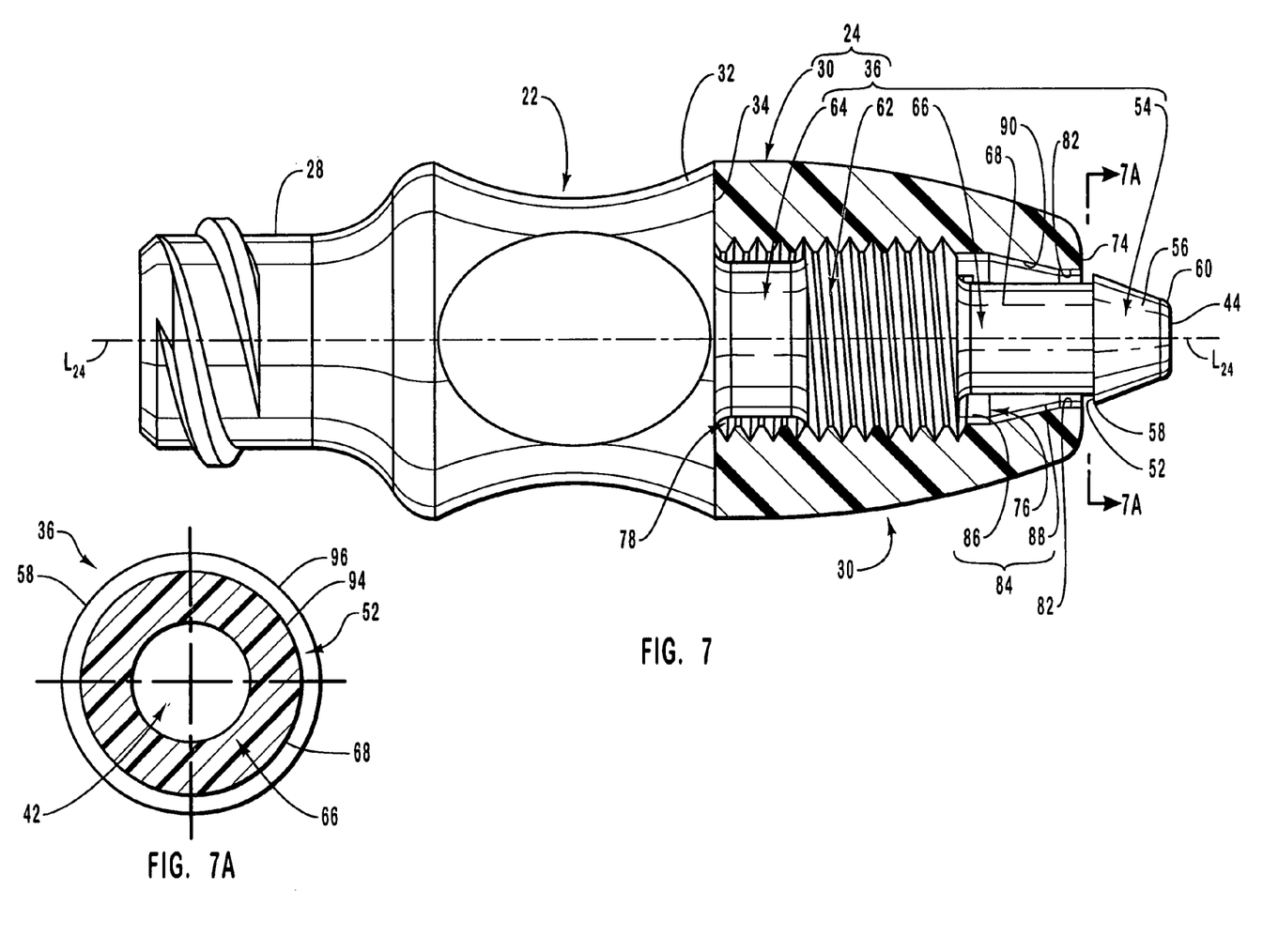
FIG. 7 is an enlarged plan view of the connection stem of FIG. 3 with the securement collar of FIG. 6 in cross section secured thereto in the assembled condition of the catheter connection system of FIG. 1.
FIG. 7A is an enlarged elevation view in cross section of the distal end of the connection stem of the catheter connection system shown in FIG. 7 taken along section line 7A-7A therein.

To assemble securement collar 30 to connection stem 36, proximal face 72 of securement collar 30 is advanced over the exterior of connection stem 36 until second set of threads 78 engages first set of threads 62. Thereafter, relative rotation of securement collar 30 about connection stem 36 advances proximal face 72 of securement collar 30 into engagement with distal face 34 of coupling hub 22 as shown in FIG. 7. There, in the assembled condition of catheter connection system 24, longitudinal axis $L_{30}$ of securement collar 30 coincides with longitudinal axis $L_{36}$ of connection stem 36, together defining a longitudinal axis $L_{24}$ of catheter connection system 24. In FIG. 7, locking ring 82 on securement collar 30 is positioned proximal of shoulder 58 of barb 54.

In the assembled condition of catheter connection system 24, internal bore 76 of securement collar 30 cooperates with exterior surface 68 of shaft 66 of connection stem 36 to form a void 84 that encircles connection stem 36 interior of catheter connection system 24. Void 84 has an enlarged closed proximal end 86 and a smaller distal end 88 opening to the exterior of catheter connection system 24 between locking ring 82 and exterior surface 68 of shaft 66. The portion of internal bore 76 of securement collar 30 between locking ring 82 and second set of threads 78 assumes the form of a purchase enhancement region 90 that is provided with an internal diameter that increases in a proximal direction longitudinally along longitudinal axis $L_{24}$ of catheter connection system 24 more rapidly than any increase in the outer diameter of the exterior of connection stem 36 opposite thereto. As exterior surface 68 of shaft 66 is cylindrical, void 84 illustrated in FIG. 7 has a constant inner diameter corresponding to exterior surface 68 of shaft 66 and a minimum outer diameter where distal end 88 of void 84 opens to the exterior of catheter connection system 24.

By reference to FIGS. 7 and 7A taken together, it will be observed that barrier wall 52 of enlargement 48 on connection stem 36 is a flat, annular surface disposed in a plane P that is oriented perpendicular to the longitudinal axis of connection stem 36, which in turn is coincident with longitudinal axis $L_{24}$ of catheter connection system 24. Consequently, barrier wall 52 has a circular inner periphery 94 and a concentric outer periphery 96. Outer periphery 96 is coincident with shoulder 58 of barb 54, while inner periphery 94 is of the same size and shape as exterior surface 68 of shaft 66.

Finally, it should be noted that securement collar 30 and connection stem 36 do not require adhesive and are reusably disassemblable out of the assembled condition of catheter connection system 24 illustrated in FIG. 7.

The process of attaching distal portion 16 of catheter tube 14 to coupling hub 22 using the components of catheter connection system 24 is depicted in the sequence of steps illustrated in FIGS. 8A-8E.

Figure 8A:
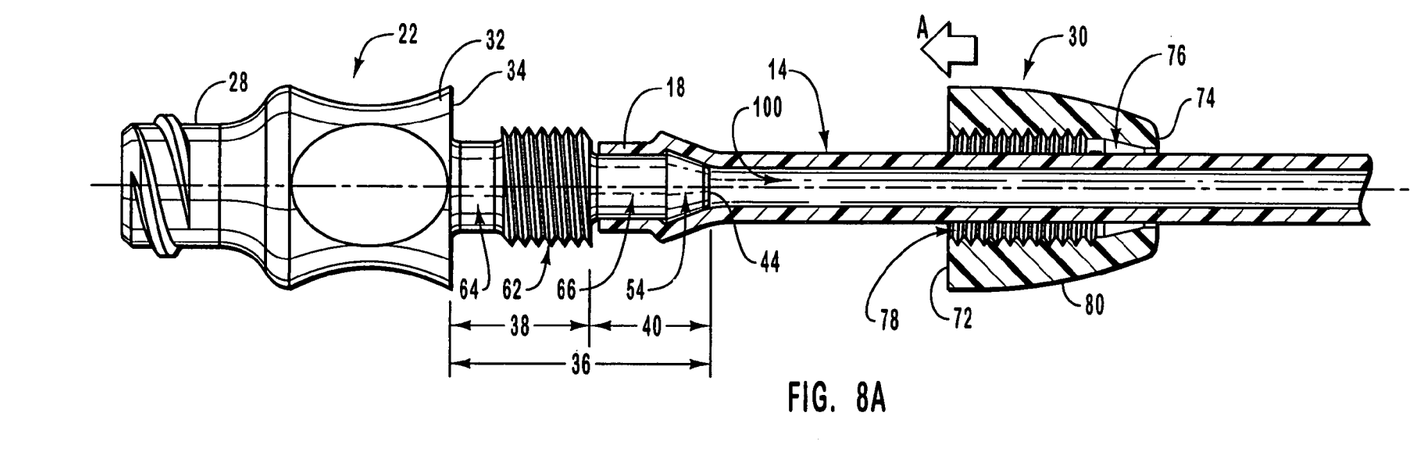
FIGS. 8A-8E are diagrams in partial longitudinal cross section illustrating steps used to attach components of the catheter connection system of FIG. 7 to the proximal end of the catheter tube of the catheter device of FIG. 1.
Figure 8B:
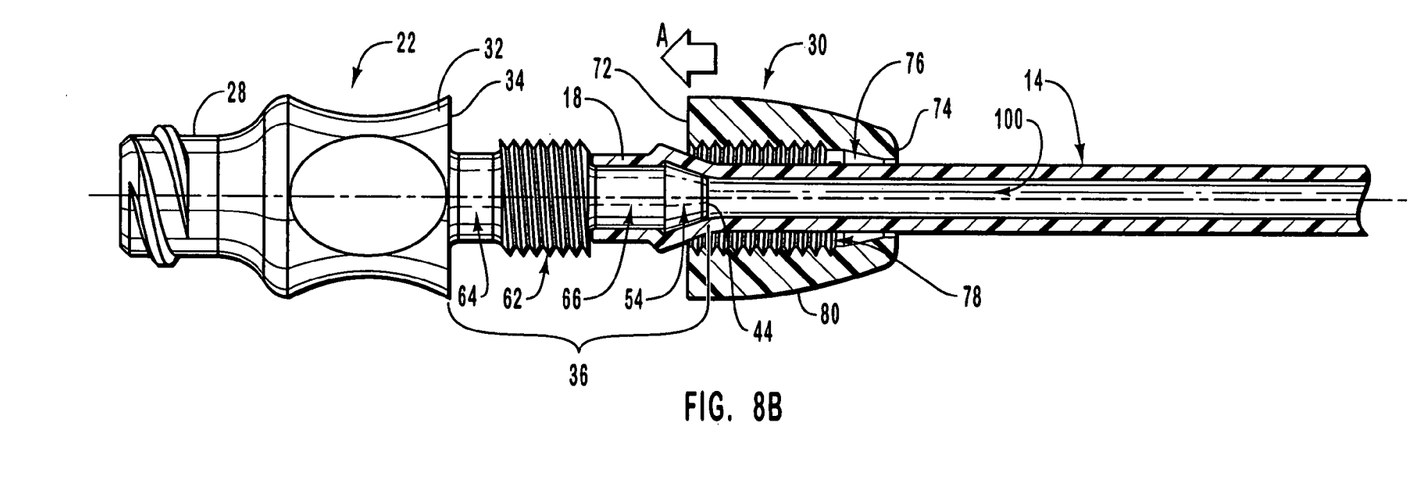

As depicted in FIG. 8A, proximal end 18 of catheter tube 14 is passed through internal bore 76 of securement collar 30 and then advanced over barb 54 and shaft 66 of connection stem 36 toward first set of threads 62. As a result, the walls of proximal end 18 of catheter tube 14 are stretched radially outwardly by the external features on the portion of distal end 40 of connection stem 36 received in lumen 100 of catheter tube 14. Securement collar 30 is then advanced along the exterior of catheter tube 14 toward coupling hub 22 in a direction indicated by arrow A in FIGS. 8A and 8B.

Figure 8C:
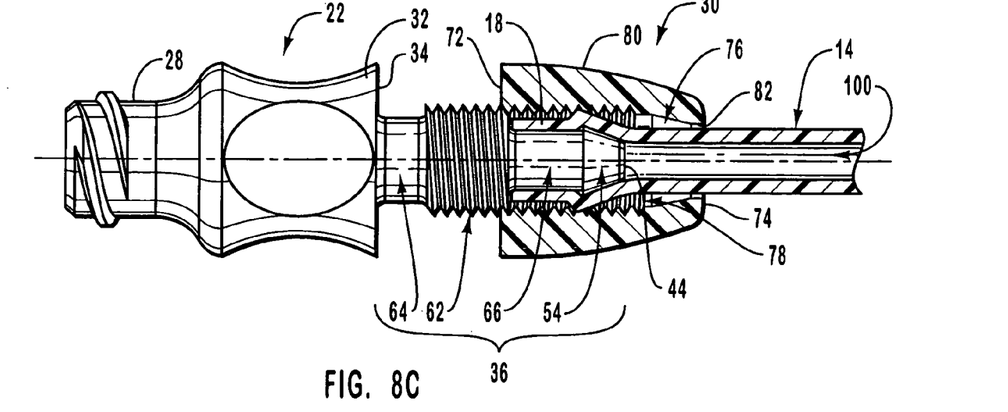

Continued movement of securement collar 30 in the direction indicated by arrow A will bring second set of threads 78 at proximal face 72 of securement collar 30 into engagement with first set of threads 62 on the exterior of connection stem 36. Such a situation is illustrated in FIG. 8C. As appreciated therein, the portion of securement collar 30 on which second set of threads 78 is formed has an internal diameter sufficiently large to pass freely along the exterior of proximal end 18 of catheter tube 14, even with connection stem 36 received in lumen 100 thereof.

Figure 8D:
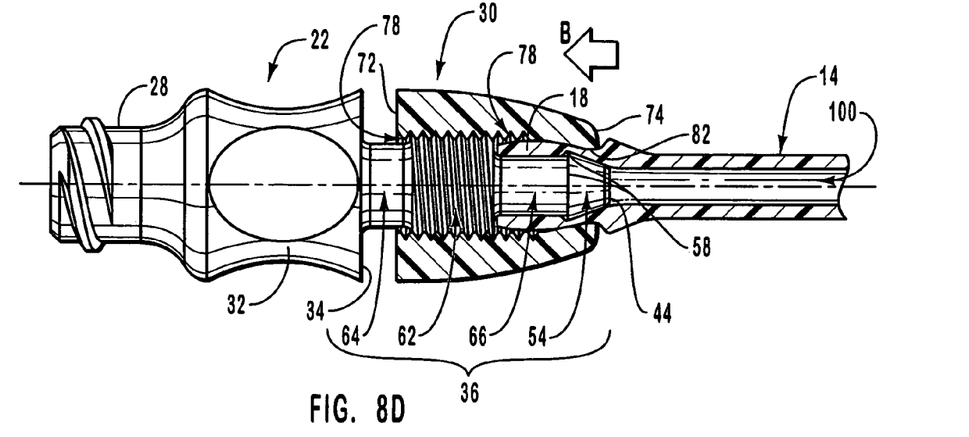

Securement collar 30 is then rotated about connection stem 36, mating second set of threads 78 on securement collar 30 with first set of threads 62 on the exterior of connection stem 36, imparting translational movement to securement collar 30 and advancing securement collar 30 toward coupling hub 22 in a direction indicated in FIG. 8D by arrow B. In so doing, locking ring 82 on the interior of securement collar 30 adjacent to distal face 74 is eventually drawn into compressive engagement with proximal end 18 of catheter tube 14 at shoulder 58 of barb 54. There, the clearance between locking ring 82 and the exterior features of connection stem 36 is a minimum. Accordingly, the material properties of the material chosen for catheter tube 14 should be such as to endure temporary radial compression against shoulder 58 of barb 54 in this manner without damaging the material integrity of catheter tube 14. Several medical grades of polyurethane are possessed of such material properties.

Figure 8E:
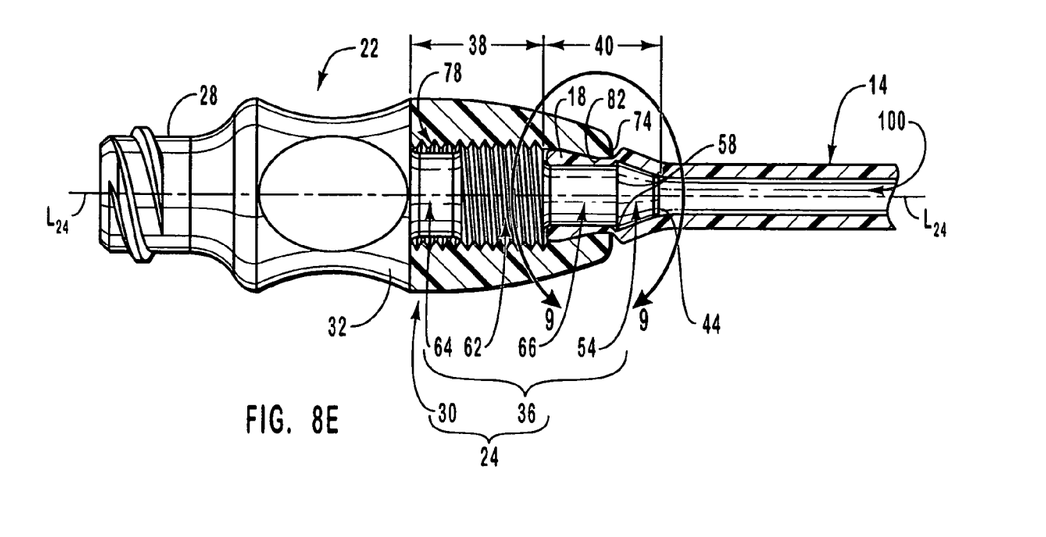

The continued rotation of securement collar 30 about connection stem 36 will eventually advance proximal face 72 of securement collar 30 longitudinally into abutment with distal face 34 of coupling hub 22 as shown in FIG. 8E. FIG. 8E thus depicts the assembled condition of catheter connection system 24 with distal end 40 of catheter connection stem 36 received in lumen 100 of catheter tube 14.

In assuming the assembled condition of catheter connection system 24, locking ring 82 on the interior of securement collar 30 is drawn to the proximal side of shoulder 58 of barb 54, thereby to compress proximal end 18 of catheter tube 14 radially inwardly against shaft 66 of connection stem 36. The radial compression of proximal end 18 of catheter tube 14 against shaft 66 in this manner is, nonetheless, less intense than the compression of proximal end 18 effected temporarily between locking ring 82 and shoulder 58 of barb 54 as securement collar 30 is being advanced into the assembled condition of catheter connection system 24. As a result, the backwards threading of securement collar 30 out of the assembled condition of catheter connection system 24 is resisted, and securement collar 30 tends to remain biased into the assembled condition of catheter connection system 24 shown in FIG. 8E.

Figure 9:
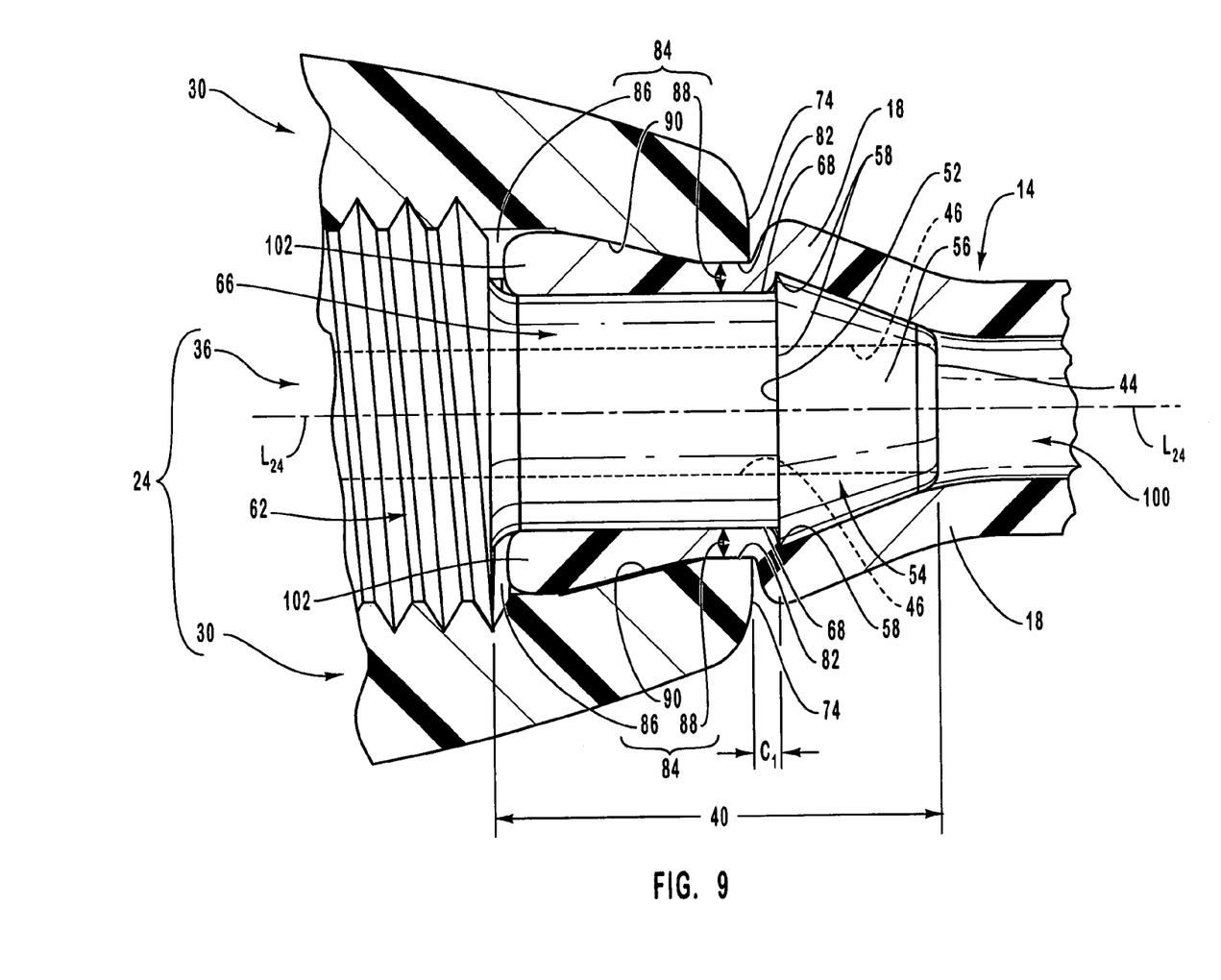
FIG. 9 is an enlarged detail in partial longitudinal cross section illustrating the interrelationship of the components of the catheter connection system of FIG. 7 when attached to the proximal end of a catheter tube in the manner shown in FIG. 8E.

The relative relationship of selected elements in the assembled condition of catheter connection system 24 with distal end 40 of connection stem 36 received in lumen 100 of catheter tube 14 is illustrated in enlarged detail in FIG. 9. Several features of catheter connection system 24 are thus revealed that contribute to securely attaching catheter tube 14 in fluid communication with coupling hub 22.

Thus, a catheter connection system according to teachings of the present invention is provided with pinching means for urging a portion of the outer wall of catheter tube 14 against exterior surface 68 of shaft 66 to create in that portion of the outer wall of catheter tube 14 longitudinally uniform conditions of maximum compression produced in the outer wall of catheter tube 14 by catheter connection system 24. As shown by way of example and not limitation, locking ring 82 is provided on the interior of securement collar 30 adjacent to distal face 74 thereof. Locking ring 82 includes a cylindrical interior surface adjacent to and proximal of distal face 74 having a radius greater than outer periphery 96 of barrier wall 52 shown in FIG. 7A. The inner diameter of internal bore 76 in securement collar 30 is minimized at the cylindrical interior surface of locking ring 82, and locking ring 82 in the assembled condition of catheter connection system 24 is positioned proximal of shoulder 58 of barb 54 concentrically encircling the cylindrical exterior surface 68 of shaft 66.

The creation of a region of longitudinally uniform conditions of maximum compression in the outer wall of catheter tube 14 enhances the reliability of the attachment to coupling hub 22 effected by the assembled elements of catheter connection system 24. The region of longitudinally uniform maximum compression in the outer wall of catheter tube 14 eliminates uneven radially differential stresses in proximal end 18 of catheter tube 14 for a finite longitudinal distance. Doing so at the location at which proximal end 18 of catheter tube 14 is gripped with maximum intensity by the assembled elements of catheter connection system 24 reduces the creep of the material of catheter tube 14 away from that secure grip.

As further observed in FIG. 9, the configuration of void 84 formed internally of catheter connection system 24 causes proximal end 18 of catheter tube 14 proximal of locking ring 82 to form an enlarged securement lip 102 that encircles shaft 66 of connection stem 36, substantially filling void 84. Therefore, according to yet another teaching of the present invention, a catheter connection system, such as catheter connection system 24, is provided with purchase enhancement means for retaining a securement lip of catheter material from the outer wall of catheter tube 14 internal of the catheter connection system in the assembled condition thereof. As shown by way of example and not limitation, purchase enhancement region 90 located proximal of locking ring 82 interior of securement collar 30 cooperates with exterior surface 68 of shaft 66 of connection stem 36 to cause void 84 to have an enlarged closed proximal end 86 and a smaller distal end 88 opening to the exterior of catheter connection system 24 between securement collar 30 and the exterior of connection stem 36. Securement lip 102 is less radially compressed than the portion of proximal end 18 of catheter tube 14 at locking ring 82, contributing to resisting the withdrawal of proximal end 18 of catheter tube 14 from connection stem 36.

According to yet another teaching of the present invention, a catheter connection system, such as catheter connection system 24, is provided with grip enhancement means for constraining the outer wall of catheter tube 14 to traverse a tortuous path when distal end 40 of connection stem 36 is received in lumen 100 of catheter tube 14 and securement collar 30 and connection stem 36 are in the assembled condition of catheter connection system 24. As shown by way of example and not limitation, an enlargement taking the form of barb 54 is formed on the exterior of distal end 40 of connection stem 36. Enlargement 48 terminates at proximal end 50 thereof in a barrier wall 52 that encircles connection stem 36. Correspondingly, the interior of securement collar 30 is provided with locking ring 82, which in the assembled condition of catheter connection system 24 is positioned proximal of barb 54 encircling the exterior of catheter connection stem 36.

Consequently, distally from the cylindrical interior surface of locking ring 82, the outer wall of catheter tube 14 is required to traverse a tortuous path, first turning approximately ninety degrees around the distal end of locking ring 82 to occupy a narrow channel $C_1$ between distal face 74 of securement collar 30 and barrier wall 52. Distal thereof, the outer wall of catheter tube 14 turns approximately ninety degrees in a different direction, passing over and around shoulder 58 of barb 54 and distally along the portion of outer surface 56 of barb 54 adjacent to shoulder 58. This tortuous pathway enhances the purchase of proximal end 18 of catheter tube 14 on distal end 40 of connection stem 36.

Figure 10:
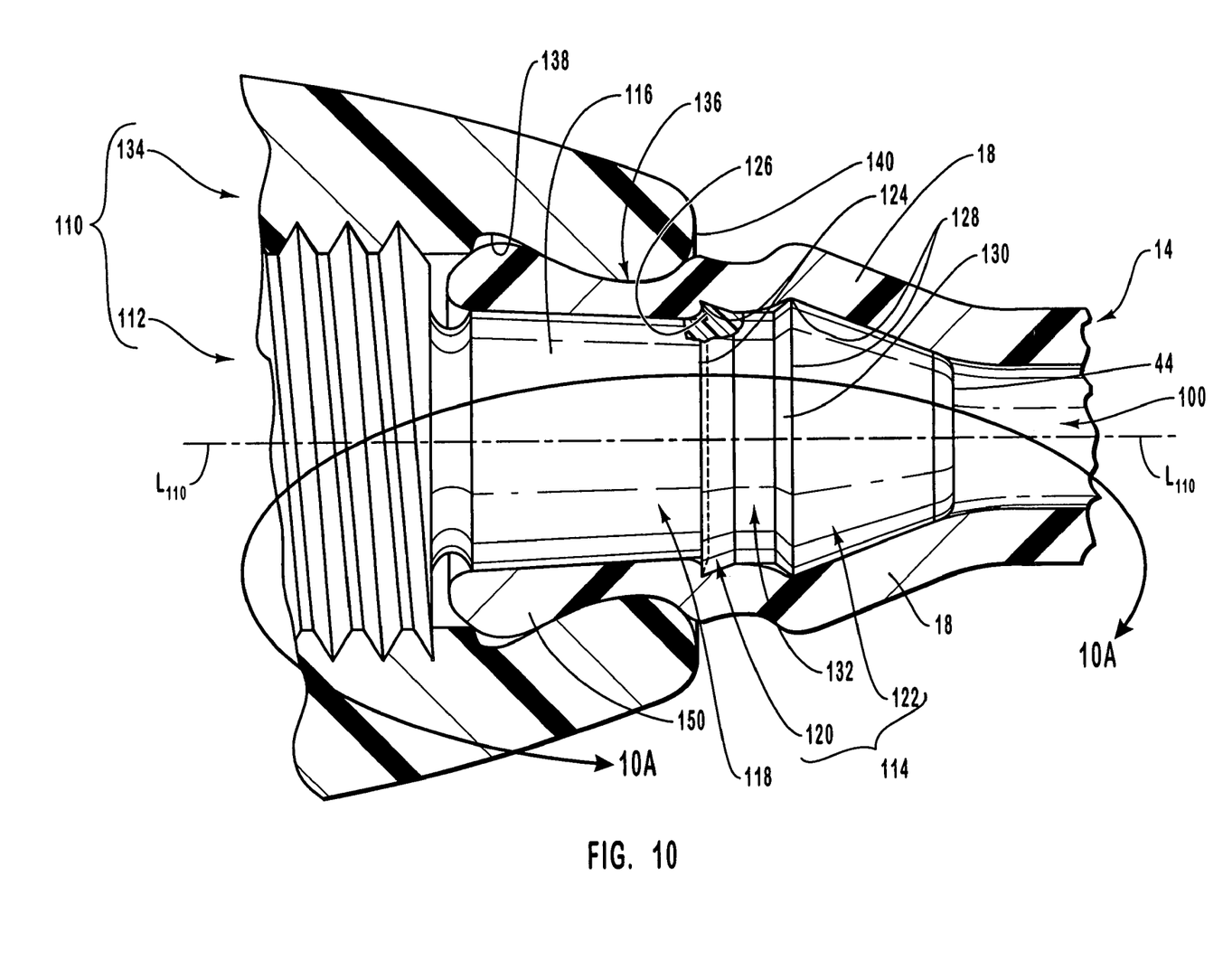
FIG. 10 is an enlarged detail in partial longitudinal cross section similar to FIG. 9 illustrating the interrelationship of the components of a second embodiment of a catheter connection system incorporating teachings of the present invention attached to the proximal end of a catheter tube.
Figure 10A:
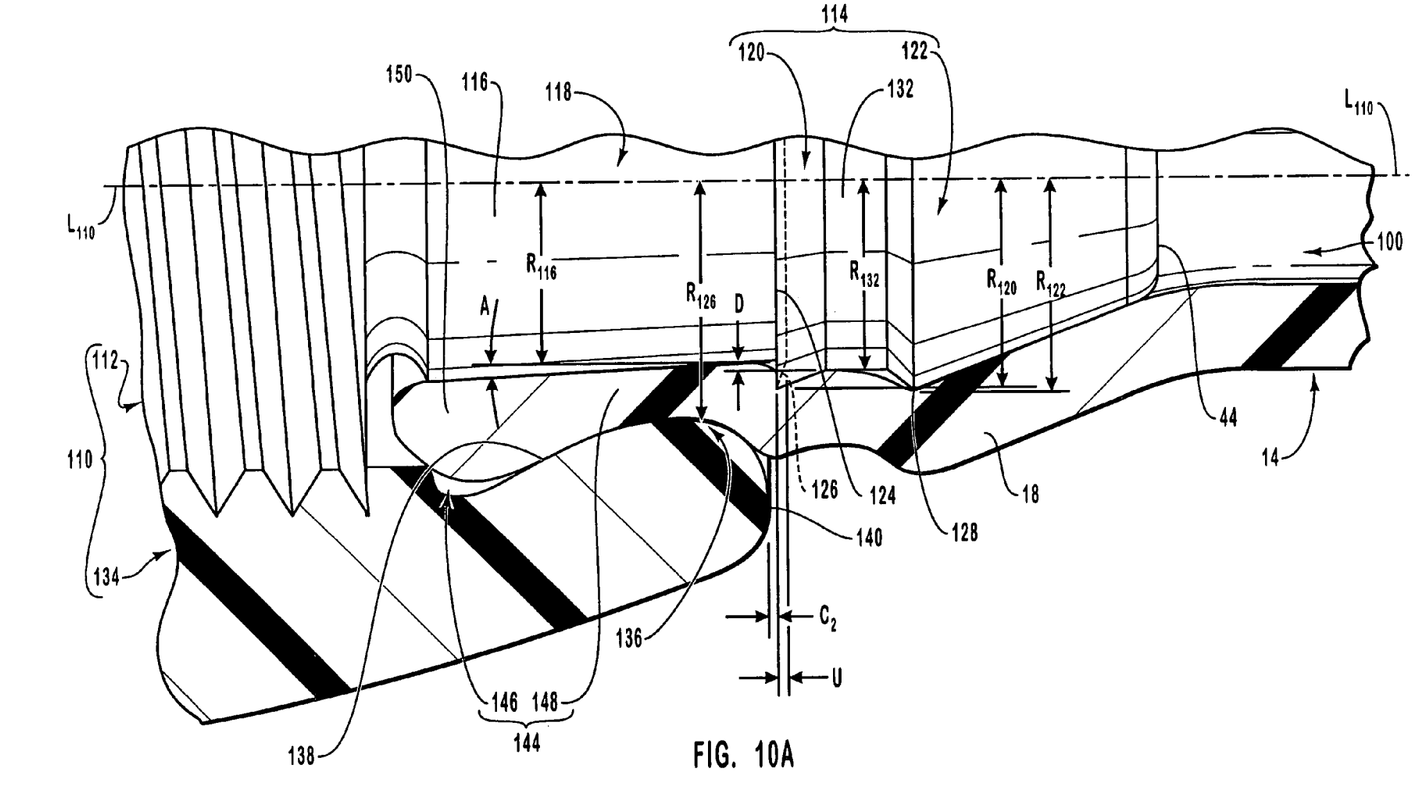
FIG. 10A is an enlarged detail in partial longitudinal cross section of a portion of the catheter connection system of FIG. 10.

FIGS. 10 and 10A taken together illustrate selected features of the assembled condition of a second embodiment of a catheter connection system 110 that embodies teachings of the present invention and that is attached to proximal end 18 of catheter tube 14.

Catheter connection system 110 includes a catheter connection stem 112 that differs in structure from catheter connection stem 36 of catheter connection system 24 due to the nature of an enlargement 114 on the distal end of catheter connection stem 112 and due to the shape of the exterior surface 116 of a shaft 118 located proximal of enlargement 114.

Enlargement 114 includes a primary barb 120 and a secondary barb 122 located distally thereof. Interposed between primary barb 120 and secondary barb 122 is a cylindrical barb interconnection stent 132 having a radius $R_{132}$ that is larger by an amount identified as difference D in FIG. 10A than the radius $R_{116}$ of exterior surface 116 of shaft 118 at the distal end thereof. Primary barb 120 terminates at a primary shoulder 124 where a barrier wall 126 forms an undercut of extent U into primary barb 120. Barrier wall 126 is a proximally facing frustoconical surface that enlarges radially outwardly in a proximal direction from the distal end of exterior surface 116 of shaft 118 to the proximal end of primary barb 120. Secondary barb 122 has a secondary shoulder 128 and a barrier wall 130 that is a generally inclined frustoconical surface enlarging radially outwardly in a distal direction from the exterior of catheter connection stem 112 to secondary shoulder 128.

As illustrated in enlarged detail in FIG. 10A, the maximum radius $R_{122}$ of secondary barb 122 is greater than the maximum radius $R_{120}$ of primary barb 120. This enables secondary shoulder 128 of secondary barb 122 to offer purchase by catheter tube 14 on catheter connection stem 112 distal of primary barb 120.

Exterior surface 116 of shaft 118 of catheter connection stem 112 differs from exterior surface 68 of shaft 66 of catheter connection stem 36 in that exterior surface 116 shown in FIG. 10A is frustoconical, tapering radially outwardly in a proximal direction from the undercut created by barrier wall 126 of primary barb 120. The radially outward taper of exterior surface 116 of shaft 118 is evidenced by a divergence angle A shown in FIG. 10A by which the profile of exterior surface 116 diverges from a line parallel to longitudinal axis $L_{110}$ of catheter connection system 110.

The second element of catheter connection system 110 is a securement collar 134 that differs in structure from securement collar 30 of catheter connection system 24 due to the shape of a locking ring 136 positioned at the distal end of securement collar 134 and due to the shape of a purchase enhancement region 138 located internal of securement collar 134 proximal from locking ring 136.

The distal extent of locking ring 136 is defined by a curved convex distal face 140 of securement collar 134, which is markedly more protuberant than distal face 74 of securement collar 30 of catheter connection system 24. Nonetheless, a narrow channel $C_2$ is maintained between primary shoulder 124 of primary barb 120 and the maximum distal extent of distal face 140 of securement collar 134 in the assembled condition of catheter connection system 110. Locking ring 136 includes an interior surface adjacent to and proximal of distal face 140 that is a continuous convex curve. Locking ring 136 thus has a minimum radius $R_{136}$ that is greater than the maximum radius $R_{122}$ of secondary barb 122.

Purchase enhancement region 138 tapers radially outwardly in a proximal direction at a faster rate than the radially outward taper of purchase enhancement region 90 of securement collar 30 of catheter connection system 24. As a result, notwithstanding the outward taper of exterior surface 116 of shaft 118 opposite purchase enhancement region 138 in the assembled condition of catheter connection system 110, the assembled elements of catheter connection system 110 produce internally thereof a void 144 encircling connection stem 112 that has an enlarged closed proximal end 146 and a smaller distal end 148 that opens to the exterior of catheter connection system 110 between the interior of securement collar 134 and the exterior of catheter connection stem 112. Thus, the material of proximal end 18 of catheter tube 14 forms an enlarged securement lip 150 that fills void 144 and enhances the reliability of the attachment of catheter connection system 110 to catheter tube 14.

Figure 11:
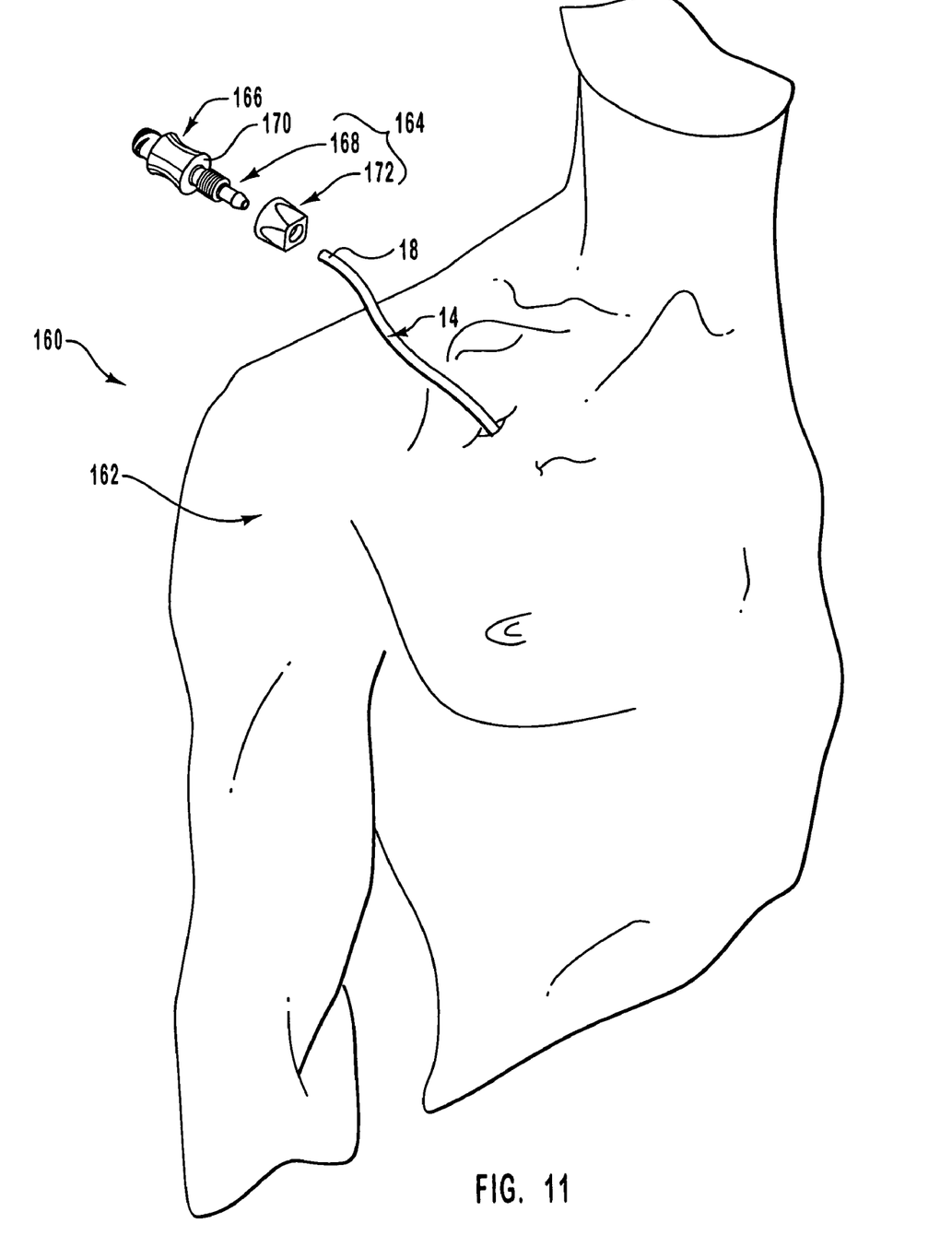
FIG. 11 is a perspective view of the extracorporeal portion of a cardiovascular access catheter implanted in the body of a patient and components of a catheter repair kit intended for attachment thereto utilizing a third embodiment of a catheter connection system incorporating teachings of the present invention.

As shown in FIG. 11, catheter connection system 24, for example, can be used as components of a kit by which to repair or extend the length of the extracorporeal portion of proximal end 18 of catheter tube 14 exiting the body of a patient 160 in the vicinity of shoulder 162 thereof. If proximal end 18 of catheter tube 14 becomes worn or compromised, the coupling hub previously attached thereto may be severed from proximal end 18 of catheter tube 14. Then the illustrated elements of a third embodiment of a catheter connection system 164 can be attached thereto substantially in the manner previously discussed in relation to FIGS. 8A-8E. The components of catheter connection system 164 include a catheter connection stem 168 projecting from the distal end 170 of a coupling hub 166 and a securement collar 172.

The assembly of a catheter connection system embodying teachings of the present invention involves no use of adhesive, and that assembly is capable of being performed in the field. Therefore, the use of a catheter connection system, such as catheter connection system 164, in a kit for servicing the extracorporeal portion of an implanted catheter affords an opportunity to extend the useful life of an implanted catheter and to avoid unnecessary explantations and reimplantations during the time that the medical procedures facilitated thereby are required by a patient.

Figure 12:
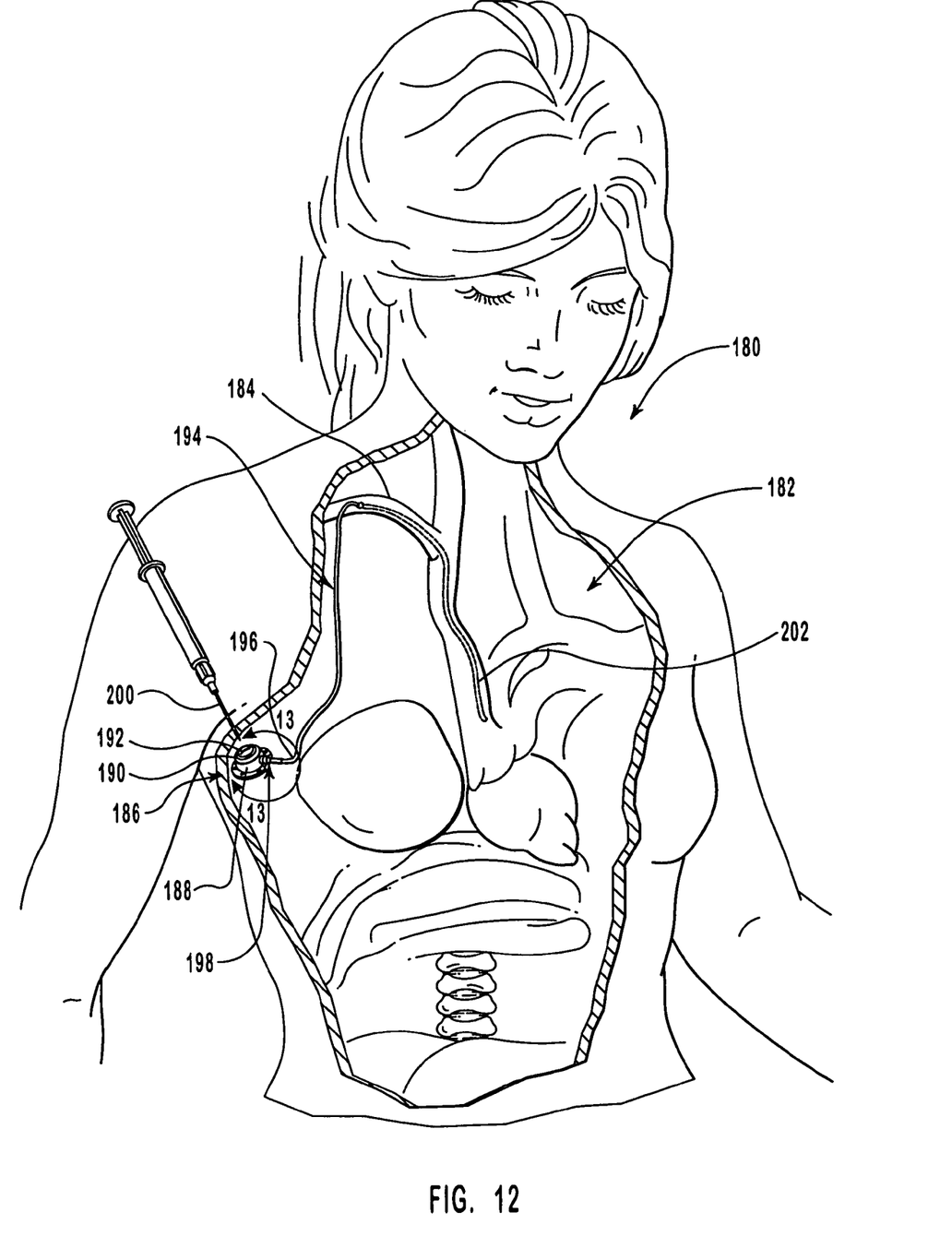
FIG. 12 is a perspective view of an access port implanted in the body of a patient connected to a cardiovascular access catheter utilizing a fourth embodiment of a catheter connection system embodying teachings of the present invention.

In yet another example of the use of a catheter connection system incorporating teachings of the present invention, FIG. 12 depicts a patient 180 having a chest 182 and a subclavian vein 184 therein. Implanted in chest 182 of patient 180 is an access port 186. Access port 186 is another example of a medical device that accommodates fluid flow and can be used with a catheter connection system embodying teachings of the present invention. Access port 186 is shown as comprising a needle-impenetrable housing 188 that is provided with an access opening 190. A needle-penetrable septum 192 is retained in access opening 190 to seal the fluid cavity.

Also implanted in chest 182 of patient 180 is an elongated catheter tube 194 having a proximal end 196 that is attached in fluid communication to access port 186 by a catheter connection system 198. Catheter tube 194 is disposed in part within subclavian vein 184. A hypodermic needle 200 can penetrate septum 192 to deliver medication to the fluid cavity of access port 186. The medication then travels through catheter connection system 198 and is discharged into the cardiovascular system of patient 180 at distal end 202 of catheter connection system 198.

Figure 13:
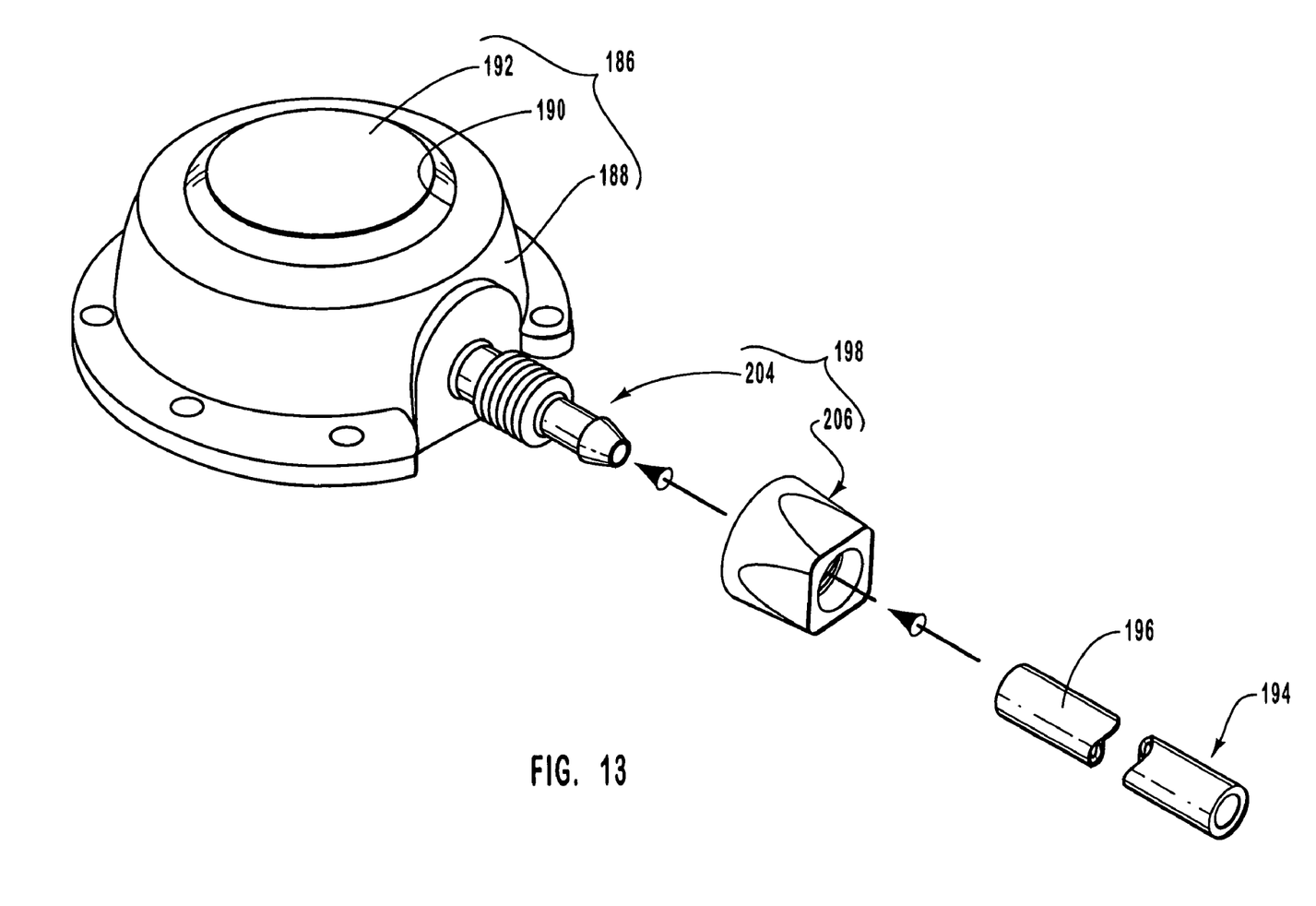
FIG. 13 is an enlarged perspective view in disassembled condition of the catheter connection system shown in FIG. 12.

FIG. 13 is an enlarged view of access port 186 with elements of catheter connection system 198 shown in disassembled condition. FIG. 13 reveals that catheter connection system 198 includes a catheter connection stem 204 that projects from housing 188 of access port 186 and a securement collar 206. These components are manipulable into the assembled condition of catheter connection system 198 with proximal end 196 of catheter tube mechanically joined thereto in a reliable fluid-tight coupling using similar steps of assembly as those illustrated in FIGS. 8A-8E.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of coupling a catheter to a stem, the method comprising:
    providing a stem extending longitudinally between a proximal end and a distal end, the stem including at least one enlargement positioned between the proximal end and the distal end of the stem;
    positioning a catheter over the at least one enlargement and over a region of the stem having a constant outside diameter that is proximal to the at least one enlargement;
    mating a first portion of a collar with the stem to thereby advance a distal end of the collar past the at least one enlargement to a position over the region of the stem that is proximal to the at least one enlargement; and
    compressing a portion of the catheter that is positioned over the region of the stem that is proximal to the at least one enlargement to generate a maximum compressive stress in the catheter adjacent to the enlargement.

2. The method of claim 1, wherein compressing the catheter comprises contacting at least a portion of an outer surface of the catheter.

3. The method of claim 1, wherein compressing the catheter comprises contacting at least a portion of an outer surface of the catheter with a ring.

4. The method of claim 3, wherein the ring exhibits an internal dimension that increases at a rate, in relation to a proximal direction along the stem, that exceeds a rate of increase of an outer dimension of the at least one enlargement.

5. The method of claim 1, wherein compressing the catheter comprises compressing radially inwardly at least a portion of the catheter.

6. The method of claim 1, wherein the collar comprises an internal bore with a proximal threaded region, an intermediate tapered region, and a distal reduced constant diameter region, and generating the maximum compressive stress in the catheter adjacent to the enlargement comprises generating a longitudinally uniform condition of maximum compression in the catheter between the stem at the constant outside diameter portion and the collar at the distal reduced constant diameter region adjacent to the enlargement.

7. A method of coupling a catheter to a stem, the method comprising:
   providing a stem extending longitudinally between a proximal end and a distal end, the stem including an enlargement positioned at the distal end of the stem;
   positioning a catheter over the enlargement and over a region of the stem that is proximal to the enlargement;
   rotating a collar into successively greater contact with the stem to move the entire collar from a position that is distal to the enlargement to a position that is proximal to the enlargement; and
   compressing the catheter against a constant outside diameter portion of the stem to generate a circumferential longitudinally uniform maximum compressive stress in the catheter adjacent to the enlargement.

8. The method of claim 7, wherein compressing the catheter against the stem comprises contacting at least a portion of an outer surface of the catheter.

9. The method of claim 7, wherein compressing the catheter comprises contacting at least a portion of an outer surface of the catheter with a ring.

10. The method of claim 9, wherein the ring exhibits an internal dimension that increases at a rate, in relation to a proximal direction along the stem, that exceeds a rate of increase of an outer dimension of the enlargement.

11. The method of claim 8, wherein contacting the at least a portion of the outer surface of the catheter comprises moving the collar longitudinally along the catheter.

12. The method of claim 7, wherein compressing the catheter against the stem comprises compressing radially inwardly at least a portion of the catheter.

13. A method of coupling a catheter to a stem, the method comprising:
   providing a stem defining a lumen and including an exterior surface, the stem including an enlargement formed on the exterior surface of the stem and a constant outside diameter shaft portion proximal to the at least one enlargement, the stem further including a threaded region;
   positioning a catheter over the enlargement and the constant outside diameter shaft portion;
   coupling a collar with the threaded region of the stem to position a distal end of the collar from a position that is distal to the enlargement to a position that is proximal to the enlargement; and
   compressing the catheter between the stem at the constant outside diameter shaft portion and a distal end of the collar to generate a maximum compressive stress in the catheter.

14. The method of claim 13, wherein compressing the catheter comprises contacting at least a portion of an outer surface of the catheter with the collar.

15. The method of claim 13, wherein the collar comprises a ring that exhibits an internal dimension that increases at a rate, in relation to a proximal direction along the stem, that exceeds a rate of increase in the outer dimension of the enlargement.

16. The method of claim 13, wherein the collar comprises a bore having a threaded end section, a tapered section, and a constant diameter end section, the constant diameter of the end section smaller than an inner diameter of the remaining bore outside of the end section, and wherein compressing the catheter comprises compressing the catheter between the constant diameter end section of the collar and the constant outside diameter shaft portion of the stem to produce the maximum compressive stress in the catheter.

17. The method of claim 1, wherein mating the first portion of the collar with the stem comprises contacting the first portion of the collar to a successively greater length of the stem.

18. The method of claim 7, wherein rotating the collar relative to the stem causes a successively larger portion of a threaded region of the collar to engage the threaded region of the stem.

19. The method of claim 13, wherein coupling a collar with the threaded region of the stem comprises advancing a first portion of the collar from a first position in the threaded region to a second position in the threaded region, wherein a second portion of the collar is distal to the at least one enlargement of the stem when the first portion of the collar is in the first position and is proximal to the at least one enlargement of the stem when the first portion of the collar is in the second position.

* * * * *